United States Patent [19]
Lebl et al.

[11] Patent Number: 5,684,131
[45] Date of Patent: Nov. 4, 1997

[54] SUBSTITUTED BENZHYDRYLAMINES AS HANDLES FOR SOLID PHASE PEPTIDE SYNTHESIS

[76] Inventors: Michal Lebl, 12460 Granville Canyon Way; Marcel Patek, 10700 N. La Reserve Dr. #16203, both of Tucson, Ariz. 85737

[21] Appl. No.: 137,048

[22] PCT Filed: Apr. 10, 1992

[86] PCT No.: PCT/US92/02962

§ 371 Date: Jul. 5, 1994

§ 102(e) Date: Jul. 5, 1994

[87] PCT Pub. No.: WO92/18144

PCT Pub. Date: Oct. 29, 1992

[30] Foreign Application Priority Data

Apr. 12, 1991 [CZ] Czech Rep. ............... 1030-91

[51] Int. Cl.$^6$ ........................ C07K 1/04
[52] U.S. Cl. ............ 530/334; 530/333; 562/442
[58] Field of Search ............... 530/333, 334; 525/54.11; 560/27; 562/442

[56] References Cited

U.S. PATENT DOCUMENTS 3,963,701 6/1976 Grisar ........................ 260/239

FOREIGN PATENT DOCUMENTS 0239461 9/1987 European Pat. Off. .
0 331 073 9/1988 European Pat. Off. .
0 322 348 6/1989 European Pat. Off. .

OTHER PUBLICATIONS

Marshall et al., J. Org. Chem., 35:867 (1970).
Kenner et al., Chemical Commun. 636 (1971).
"The Peptide Analysis, Synthesis, Biology", E. Gross, J. Meienhofer Eds., Academic Press, New York, v.3, p.209, date not available.
Chemical Abstracts 110:135705 (1989).
Chemical Abstracts 115:183681S (1992).
Orlowski et al., J. Org. Chem. 41(23):3701–3705 (1976).
Funakoshi et al., Chem. Commun. 5:382–384 (1988).
Fields and Noble, Int. J. Pept. Res. 35:161–214 (1990).
Albercio et al., Int. J. Pept. Prot. Res. 30:206–216 (1987).
Carpino et al., Accounts of Chemical Research, 20:(11):401–407 (1987).
Patek, Tet Lett, 31, 5209, 1990.
Patek Tet Lett 32, 3891, 1991.

*Primary Examiner*—Cecilia J. Tsang
*Assistant Examiner*—David Lukton
*Attorney, Agent, or Firm*—Pennie & Edmonds

[57] ABSTRACT

The present invention is directed to a novel "handle" for solid phase peptide synthesis. The handles can be converted from a stable form to a labile form, allowing for cleavage of a peptide amide from the support after synthesis under mild conditions, and after deprotection of the amino acid side chains. The handles are based on a substituted benzhydrylamine skeleton.

12 Claims, No Drawings

SUBSTITUTED BENZHYDRYLAMINES AS HANDLES FOR SOLID PHASE PEPTIDE SYNTHESIS

FIELD OF THE INVENTION

The present invention is directed to a novel "handle" for solid phase peptide synthesis. The handles can be converted from a stable form to a labile form, allowing for cleavage of a peptide from the support after synthesis under mild conditions, and after deprotection of the protecting groups from the amino acid side chains. The handles are based on a substituted benzhydrylamine skeleton.

BACKGROUND OF THE INVENTION

As used in the art of peptide synthesis, the handle is defined as a bifunctional spacer that serves to link the peptide fragment or first amino acid to the polymer support. Many solid phase resins and handles are available in the art, as is described in Fields and Noble, 1990, Int. J. Pept. Protein Res. 35:161–214. To be useful, handles must be stable to the reaction conditions of peptide synthesis, but when the synthesis is complete, the handle needs to allow for cleavage of the peptide from the solid support.

A few handles that can be converted from a stable form of handle to a labile form have been designed and synthesized. Unfortunately, these handles have found no broad application in practice. For example, the 4-benzylthiophenyl- and 4-benzylsulfonyl-handle (D. L. Marshall, I. E. Liener: J. Org. Chem. 35, 867 (1970)) and sulfonamide-handle (G. W. Kenner, J. R. McDermott, R. C. Sheppard: Chem. Commun. 636, (1971)) have not found broad application. Further examples can be found in "The Peptides, Analysis, Synthesis, Biology," E. Gross, J. Meienhofer, Eds., Academic Press New York, vol. 2. p. 88 (1980), vol. 3. p. 209 (1981). Quite recently, the handle based on the 4-alkylthiobenzyl alcohol has been disclosed (EP 274,998 and EP 274,999; Chem. Abstr. 110, 135705 (1989)) and used in peptide synthesis. After reduction of the sulfoxide moiety, the 4-alkylthiobenzyl ester is cleaved to give a peptide with free carboxyl group.

The majority of aforementioned handles have, however, certain obvious limitations concerning the amino acid residues that can be affected by the conversion step. As a rule, oxidation steps cannot be used when the peptide contains sensitive amino acids such as tryptophan, cysteine, cystine, and methionine. Another problem is possible methylation during "activation" of handle and long cleavage times which can cause the damage of peptide.

Moreover, the handles presently available are not well adapted to both Boc and Fmoc synthetic procedures.

SUMMARY OF THE INVENTION

The instant invention is directed to substituted benzhydrylamine handles for peptide synthesis. The handles are prepared and used in acid labile form or in stable form. The stable form can be converted to an acid labile form for cleavage of the peptide from the resin.

The substituted benzhydrylamine handles are of the general formula (I):

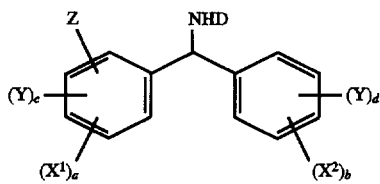

in which a=1 to 3, $X^1$ is —$GR^1$ or $X^1$ is Z, the $X^1$ groups are in the ortho or para positions of the first benzene ring, and $R^1$ is a hydrocarbon group and in which b=0 to 3, $X^2$ is —$GR^2$, the $X^2$ groups are in the ortho or para positions of the second benzene ring, and $R^2$ is a hydrocarbon group; and in which Z is $R^3$, $OR^3$ or —$GR^3$ in any position not occupied by $X^1$ unless $X^1$ is Z, and $R^3$ is a hydrocarbon group comprising a reactive functional group for coupling to a solid phase support, and in which if $X^1$ is Z, Z is —$GR^3$ in an ortho or para position; and in which c=0 or 1 and d=0 or 1, Y is $OR^4$, and $R^4$ is a hydrocarbon group; and in which —G is —S—, —SO— or —$SO_2$—; and in which D is H, a protecting group or an $N^\alpha$-protected acyl. As used herein, "hydrocarbon" can be a $C_1$ to $C_{10}$.

Further provided are methods for synthesis of the handles of the invention. In one embodiment, hydroxy or mercapto benzophenones are reacted with ω-haloesters of alkanecarboxylic acids in the presence of fluoride ions. The benzophenone carbonyl is subsequently converted to an amine by routine synthetic methods, e.g., reaction with hydroxylamine to yield an oxime, followed by reduction, e.g., with zinc, to yield benzhydrylamine, or by reductive amination, e.g., by reaction with ammonium formate. Alternatively the benzophenone can be reduced to the alcohol and amidated with an $N^\alpha$-protected amino acid amide.

The present invention offers distinct advantages over earlier methods of creating stable handles for peptide synthesis that can be treated after the synthetic reaction is complete to make the handle labile. Once the handle is converted from stable form to labile form, the peptide can be conveniently cleaved from a solid phase support and used. The peptide is cleaved in a carboxy amide (rather than free carboxyl) form. The oxidized handles, i.e., in the sulfoxide or sulfone form, are extraordinarily stable in acidic media, e.g., trifluoroacetic acid, as well as conditions generally used in peptide synthesis. When reduced to sulfide form, the handle is acid labile. In a preferred embodiment, the sulfoxide or sulfone is readily reduced to sulfide, to convert the stable handle to a labile form.

One particular advantage of the handles of the invention is that they allow for deprotection of the amino acid side chains prior to cleavage. Under standard solid phase synthesis, the cations generated during deprotection and cleavage are available to react with the cleaved peptide. Often reaction of these cations with the peptide results in decreased yield and purity. According to the present invention, the cations generated during deprotection can be washed away since the deprotected peptide remains on the solid support. During cleavage, the cations remain with the solid support, away from the cleaved peptide.

Another advantage of the invention is that cleavage of the peptide after reduction of the handle can be performed under much milder conditions than are generally available. For example, in a standard Boc synthesis cleavage requires treatment with the powerful acid, usually HF. The present invention thus allows a Boc synthesis with the final cleavage under much milder conditions.

Yet a further advantage of the invention is that the handle can be used for both Fmoc and Boc synthetic strategies.

Yet another advantage of the handles of the invention is that cleavage yields a C-terminal peptide amide under less drastic conditions than are currently available.

DETAILED DESCRIPTION OF THE INVENTION

The present invention is directed to handles for peptide synthesis that are stable, but that can be converted to labile form for subsequent cleavage of the peptide from the solid phase support. The stability of the handles is determined by the oxidation state of a thioether substituent.

The substituted benzhydrylamine handles are of the general formula (I):

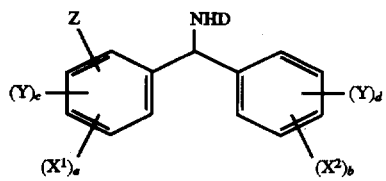

in which a=1 to 3; $X^1$ is —$GR^1$ or $X^1$ is Z, the $X^1$ groups are in the ortho or para positions of the first benzene ring, and $R^1$ is a hydrocarbon group; and in which b=0 to 3, $X^2$ is —$GR^2$, the $X^2$ groups are in the ortho or para positions of the second benzene ring, and $R^2$ is a hydrocarbon group; and in which Z is $R^3$, $OR^3$ or —$GR^3$ in any position not occupied by $X^1$ unless $X^1$ is Z, and $R^3$ is a hydrocarbon group comprising a reactive functional group for coupling to a solid phase support, and in which if $X^1$ is Z, Z is —$GR^3$ in an ortho or para position; and in which c=0 or 1 and d=0 or 1, Y is $OR^4$, and $R^4$ is an alkyl a hydrocarbon group; and in which —G is —S—, —SO— or —$SO_2$—; and in which D is H, a protecting group or an $N^\alpha$-protected acyl. As used herein, "hydrocarbon" can be a $C_1$ to $C_{10}$.

As used herein, the term hydrocarbon includes but is not limited to $C_1$ to about $C_{10}$ alkane, alkene and alkyne (i.e., saturated and unsaturated hydrocarbons). For example, a hydrocarbon group may be methyl, ethyl, ethenyl, propyl, propenyl, propynyl, etc. The term hydrocarbon as used herein includes branched chain as well as linear chain groups, and cyclic hydrocarbon.

As used herein, the term "handle" is defined as a bifunctional spacer. The handle has one functional group that binds to a solid phase support. The handle has an second functional group that can be conjugated to an amino acid or a peptide. The handle provides for cleavage of the peptide after synthesis is complete.

As used herein, the term "solid phase support" is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various synthetic protocols. For example, for peptide synthesis, solid phase support may refer to resins such as p-methylbenzhydrylamine (pMBHA) resin (Peptides International, Louisville, Ky.), polystyrene (e.g., PAM-resin obtained from Bachem Inc., Peninsula Laboratories, etc.), poly (dimethylacrylamide)-grafted styrene co-divinyl-benzene (e.g., POLYHIPE® resin, obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.).

In one embodiment, the solid phase support may be suitable for in vivo use, i.e., it may serve as a carrier for or support for direct applications of the peptide (e.g., TentaGel, Rapp Polymere, Tubingen, Germany). In a particular embodiment, the solid phase support may be palatable and orally consumable.

The term "peptide" is used herein in its broadest sense to refer to a compound of two or more subunit amino acids, amino acid analogs or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D and L optical isomers, and amino acid analogs and peptidomimetics. As used herein, a peptidomimetic is a molecule that exhibits properties similar to a peptide without having a peptide chemical structure. The peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, by assigning specific amino acids at specific coupling steps, peptides with α-helices, β turns, β sheets, γ-turns, and cyclic peptides can be generated.

4.1. HANDLES

The benzhydrylamine handles of the invention are substituted with at least one sulfur-containing derivative selected from the group consisting of sulfide ($SR^1$), sulfoxide ($SOR^1$), and sulfone ($SO_2R^1$), in which $R^1$ is a hydrocarbon group of 1 to about 10 carbon atoms. The sulfide, sulfoxide or sulfone derivative is designated throughout this application as —GR. The sulfur-containing group is found at the ortho position or para position on at least one benzene ring. Two sulfur-containing groups on a single benzene ring can be found at the ortho-para or both ortho positions. Three sulfur containing groups can be found at the two ortho and one para positions. The benzene rings can be symmetrically substituted with sulfur-containing groups, but need not be. Preferably both benzene rings contain a sulfur-containing group at the para or ortho position.

The handle further comprises a linker, Z, for attachment to a solid phase support, i.e., resin, for solid phase peptide synthesis using the handle. In one embodiment, the linker can be a sulfur-containing group (—$GR^3$) located in the ortho or para position of one benzene ring. In another embodiment, the linker can be a hydrocarbon group ($R^3$), ether ($OR^3$) group, or sulfur containing group (—$GR^3$) located at the ortho, para or meta position, with the proviso that if Z contains O or S and is in the meta position, it cannot be considered to influence the stability properties of the handle. The alkyl group on Z, $R^3$, has from 1 to about 10 carbon atoms, and comprises a functional group, for example, carboxylic acid, for attachment to the resin.

In a further embodiment, the handle comprises an ether group ($OR^4$), Y, in the ortho or para positions on one or both benzene rings not occupied by a sulfur-containing group X. No group Y is found on a ring that has Z in the ortho or para position when Z is $OR^3$ (ether). The ether groups can be but need not be symmetrically arranged on the two benzene rings. If an ether group (Y) is present, the number of Y groups on a single benzene ring is less than or equal to the number of X groups on the ring; the total number of Y is less than or equal to the total number of X groups on the benzhydryl amine, and is preferably less. The hydrocarbon portion of Y has 1 to about 10 carbon atoms.

Although the present invention is not limited to any particular mechanism, it is believed that the properties of the handle are determined by the electron donating or electron withdrawing characteristics of substituents in the ortho or para positions of the benzene ring or rings. Thus when electron donating groups, such as sulfide or ether groups, are in the para or ortho positions, acidolysis of the N—C bond readily occurs because electrons can be donated to stabilize the resulting benzhydryl cation. Conversely, when an electron withdrawing group such as sulfoxide or sulfone is present in the para or ortho positions, acidolysis cannot occur. Since electron donation occurs less readily from the meta position, substituents in the meta position are expected to have orders of magnitude less effect than substituents in the para or ortho positions.

Substitution with both sulfoxide or sulfone substituents and ether substituents results in a balance of electron withdrawing and electron donating groups. However, when the number of electron withdrawing oxidized sulfur-containing groups is at least equal to and preferably greater than the number of ether groups, the electron withdrawing nature of the oxidized sulfur-containing groups is expected to affect the properties of the handle to a greater degree. The ether groups are advantageous for cleaving the handle after reduction of the sulfur-containing groups because of their electron donating properties.

It is believed that the stability of the oxidized handle and the acid lability of the reduced handle are enhanced by increasing the number of sulfur-containing substituents on one or both benzene rings. Thus the increased electron withdrawing nature of a handle with more than one oxidized sulfur-containing group may result in greater chemical stability of the handle. Similarly, the increased electron donating potential of more than one reduced sulfur-containing groups may facilitate cleavage under mild conditions.

Additionally, oxidation of the sulfur-containing group to yield a sulfone is expected to result in a more stable handle than oxidation to the sulfoxide because the sulfone has greater electron withdrawing properties. Since either the sulfone or the sulfoxide can be reduced to yield a sulfide, either oxidation state is suitable for handles of the invention. Presently, the sulfoxide oxidation state is preferred.

In a further embodiment, the handle can be prepared with a protecting group at the amine nitrogen. Suitable protecting groups include tert-butoxycarbonyl (Boc) and N-9-fluorenylmethyloxy carbonyl (Fmoc), to name a few. Any amine protecting group suitable for peptide synthesis is suitable. Many are described in Greene and Wuts, *Protective Groups in Organic Synthesis*, Wiley Interscience: New York, 1991, pp. 309–362; and Fields and Noble 1990, Int. J. Pept. Protein Res. 35: 161–214. The N-protected benzhydrylamine can be coupled to the solid support without concern for reactivity of the amine group. After the handle is coupled to the solid support, the protecting group can be removed by routine chemistry, e.g., treatment with piperidine in dimethylformamide in the case of Fmoc, or treatment with trifluoracetic acid in the case of Boc.

In another embodiment, the handle can be prepared as a benzhydrylamide, i.e., with an acyl group on the amine. Acyl groups for use in the invention include but are not limited to $N^\alpha$-protected amino acids, which can be deprotected for subsequent elongation of a peptide chain. The term amino acids is used here as defined above, and includes D and L amino acids, glycine, and non-naturally occurring amino acids or amino acid analogs.

When X (or Z) is found as a sulfoxide or sulfone group on the handle, the handle is extremely resistant to acidic media. Reduction of a sulfoxide or sulfone to a sulfide yields a handle that is labile to acidolysis. For example, such a handle can be cleaved in trifluoroacetic acid. Thus, the present invention provides handles that are acid stable or acid labile, and provides for conversion of the acid stable form to the labile form, and vice versa.

4.2. SYNTHESIS OF SUBSTITUTED BENZYHDRYLAMINES

The substituted benzhydrylamines of the present invention can be prepared according to the following methods.

4.2.1. PREPARATION OF BENZOPHENONES

Substituted benzophenones for use as starting materials for synthesis of handles of the invention can be prepared synthetically, for example by a condensation reaction of a substituted benzoic acid with a substituted benzene, i.e., acylation of benzene.

Suitable substituted benzoic acids include but are not limited to a 2-alkylthiobenzoic acid, 4-alkylthiobenzoic acid, 2,4-di(alkylthio)benzoic acid, 2,4,6-tri(alkylthio)benzoic acid, 2-(or 4-) alkylthio-4(or 2-)alkoxybenzoic acid, 2,4-(or 2,6-alkylthio)-6(or 4)-alkoxybenzoic acid, and the like. Moreover, the benzoic acid may be substituted at the 2,3 or 4 position with a hydrocarbon group comprising a functional group for coupling to the solid phase support (i.e., Z). Special care must be taken to protect the functional group present on the hydrocarbon group to prevent its reaction during formation of the benzophenone. For example, if the functional group is a carboxylic acid, it must be protected from reaction with thionyl chloride. Alternatively the benzoic acid can be substituted at the 2, 3 or 4 position with a hydroxy or mercapto (i.e., sulfhydryl) group. The hydroxy or mercapto group is preferably at the 2 or 4 position. If the substituted benzoic acid includes a 2 or 4 mercapto substituent, it need not include an alkylthio substituent since upon alkylation, the mercapto group will become an alkylthio group with the required properties. In a specific embodiment, the substituted benzoic acid is 2-hydroxy-4-(methylthio)benzoic acid.

Suitable substituted benzene groups include but are not limited to alkylthiobenzene (e.g., thioanisole), 1,3-dialkylthiobenzene, 1,3,5-trialkylthiobenzene, 3-alkoxy-alkylthiobenzene (e.g., 3-alkoxythioanisole), 5-alkoxy-1,3-dialkylthiobenzene and 3-alkoxy-1,5-dialkylthiobenzene. In a specific embodiment, the substituted benzene is thioanisole.

In a further embodiment, if the benzoic acid lacks hydrocarbon group for use as a linker, and lacks a hydroxy or mercapto group suitable for alkylation to attach the linker, the substituted benzene can include either of these groups.

Many variations are possible for the substituted benzoic acid and substituted benzene that can be used to prepare the benzophenone. Although many combinations and permutations are possible, and are contemplated by the instant invention, often the simplest starting materials are preferred, since these are generally less expensive, easier to obtain, and less susceptible to undesirable side reactions. Thus, the substituted benzoic acid and substituted benzene chosen must form a benzophenone with at least one sulfur-containing substituent in a para or ortho position on a benzene ring, preferably a sulfur-containing substituent on both benzene rings, and a linker or a functional group suitable for attachment of a linker.

In a specific embodiment, infra, a substituted benzoic acid is heated in thionyl chloride to yield the corresponding benzoic acid chloride. Generally this reaction can be run by heating the benzoic acid in about two molar equivalents of thionyl chloride to about 40° C. for about 10 min to about 30 min with stirring. The benzoyl chloride is then dissolved (at about 0.1 to about 1M) in an aprotic solvent, e.g., ethylene dichloride, at about 40° C. This solution is mixed with an equimolar amount of a substituted benzene, e.g., thianisole, dissolved at about 0.2 to about 3M in an aprotic solvent, (e.g., dichloroethane). The mixture is cooled to 0° C., and treated with an equivalent of aluminum chloride. The reaction mixture is allowed to warm to about 20° C., at which point a second equivalent of $AlCl_3$ can be added while temperature is controlled. The reaction mixture is stirred for about 1 to 2 hours at about 40°-50° C., and worked up by standard methods, e.g., extraction, recrystallization, etc.

It is also contemplated that a benzophenone can be modified by addition of sulfur-containing groups to the ortho or para positions, or by substitution of sulfur for oxygen in ether-substituted benzophenones. The exchange of a sulfide for an ether group occurs by treatment of the hydroxy group with chlorodimethylthiocarbamate followed by thermal rearrangement and S-alkylation. This alternative, however, requires use of an asymmetrically substituted benzophenone to provide for attachment of, or alternatively to act as, a single linker for attachment to the solid phase support.

4.2.2. ALKYLATION OF HYDROXY OR MERCAPTO-SUBSTITUTED BENZOPHENONES

In the case in which the benzophenone is prepared without a hydrocarbon linking group, alkylation to add the linking group is required. Any alkylation procedure known in the art can be used in the practice of the instant invention. These alkylation procedures are accomplished by activation of a hydrocarbon with a halogen, especially bromine or chlorine, or with another good leaving group. However, where alkylation at the ortho position is contemplated, an agent must be added to disrupt hydrogen bonding. In a preferred embodiment, the agent is fluoride ion (F).

In a specific embodiment, a substituted benzophenone is dissolved in a polar aprotic solvent. The benzophenone is substituted with a hydroxy or mercapto (SH) group at the 2, 3 or 4 position on one benzene ring. Preferably the concentration of the benzophenone is 5 mM to 1M, more preferably 50 mM to 0.5M. The optimal concentration depends on the choice of polar aprotic solvent, and the solubility of the benzophenone therein. Suitable solvents include but are not limited to acetonitrile, dimethyl formamide, dioxane, and the like, as well as mixtures thereof.

When the hydroxy or mercapto group is in the 2-position, fluoride ions are present in the solution to facilitate the alkylation reaction. The ions can be provided on an inert support. In a specific embodiment, infra, the fluoride is provided as a suspension of potassium fluoride on alumina. In another embodiment fluoride is provided as tetraethylammonium fluoride.

To this solution is added an alkylating agent, e.g., an ω-haloester of alkylcarboxylic acid, which can be prepared by halogenation of the corresponding commercially available alkylcarboxylic acid. In a specific embodiment, methyl bromovalerate is added. The alkylating agent is preferably added in molar excess relative to the concentration of the benzophenone, preferably greater than about a 20% excess, more preferably greater than about a 40% excess. The alkylation reaction can require at least about 96 hours for completion at room temperature. The alkylated benzophenone can be purified by routine methods, e.g., chromatography or crystallization, or it can be separated from solid materials (e.g., if alumina is present) concentrated, e.g., in vacuo, and used without further purification.

4.2.3. CONVERSION OF THE BENZOPHENONE TO A BENZHYDRYLAMINE

The carbonyl group of the substituted benzophenones is converted to an amine group. Conversion of a carbonyl to an amine can be accomplished by any method known in the art, including but not limited to oxime formation followed by reduction, or reductive amination, e.g., with ammonium formate. In a specific embodiment, infra, the benzophenone is reacted with hydroxylamine to yield an oxime. This reaction is generally performed in a polar solvent, preferably an alcohol, e.g., ethanol, although methanol, propanol, 2-propanol, etc., can also be used with the substituted benzophenone at roughly the same concentration as is used for the alkylation reaction. Anhydrous weak base, e.g., sodium acetate, can also be present. The reaction mixture is heated to reflux for about 1 to about 15 hours, preferably about 7 hours. The mixture can be left to stand, e.g., overnight, or worked up immediately. In work-up the reaction mixture can be filtered and concentrated in vacuo to yield a product that can be used without further purification.

The oxime product is dissolved in alcohol (preferably ethanol) and 25% ammonia at about a 1:3 ratio in about the same concentration as the alkylated benzophenone was used in the oxime step. To this solution is added about a 10-fold molar excess of powdered zinc. The suspension is heated to 50° C. and stirred for about 48 hours. The suspension is filtered and concentrated in vacuo to yield the substituted benzhydryl amine.

The benzyhydrylamine obtained by reduction of the oxime is sparingly soluble or insoluble in polar solvents. Moreover, when the reduction reaction is performed over zinc, zinc remains in the reaction mixture. Thus prior to oxidation of the sulfur-containing substituents (alkylsulfides) and protection of the amino group, it is necessary to purify the benzhydrylamine. Purification procedures include but are not limited to chromatography, e.g., on silica gel, recrystallization, preparative thin layer chromatography and the like.

In a specific embodiments, a recrystallization procedure is used. The insoluble benzhydrylamine is solubilized by adding toluene sulfonic acid, thus forming the acid salt of the amine. This reaction can be performed by dissolving the benzhydrylamine in an appropriate solvent, e.g., methanol, ethanol, and the like, preferably ethanol, at about 100–500 mM, preferably at about 150 mM. A saturated solution of toluenesulfonic acid (TsOH) in the solvent can be added, preferably by a controlled addition, e.g., dropwise addition. The product is dissolved in a polar, protic solvent system that includes water (e.g., an alcohol, such as methanol, and water, 3:1 v/v), and if necessary heated, to increase solubility. After the solution has cooled to about 20° C., an oxidizing agent, e.g. sodium periodate (to form the sulfoxide) or hydrogen peroxide (to form the sulfone) is added in molar excess based on equivalents of S atoms.

Typically the solvent for oxidation with hydrogen peroxide is glacial acetic acid. Precipitate formed during the sodium periodate oxidation is removed by filtration and the product concentrated.

4.2.4. PROTECTION OF THE AMINE GROUP

The present invention further provides for protection of the amine group after synthesis of the benzhydrylamine. Protection of the amine group can be important to prevent reactivity of the amine when coupling the handle to the solid support. Thus the invention provides amine-protected handles.

Preferred protecting groups for the amine are Boc and Fmoc. However, the other protecting groups, such as are described in Greene and Wuts, *Protective Groups in Organic Synthesis*, Wiley Interscience: New York, 1991, pp. 309–362; and Fields and Noble 1990, Int. J. Pept. Protein Res. 35: 161–214 are also contemplated. The synthesis of Boc and Fmoc protected amines is straightforward and well known in the art. $N^{\alpha}$-protected amino acids for peptide synthesis are usually protected with Boc or with Fmoc, depending on the synthetic strategy.

In a specific embodiment, infra, the amine is protected with an Fmoc protecting group. The pH of the aqueous solution containing benzhydrylamine is brought to about 9, any inorganic salts that have precipitated are removed by filtration, and protected Fmoc (e.g., Fmoc-H-N-hydroxy-succinimidyl ester) added. The Fmoc-benzhydrylamine is worked up using standard procedures to yield a product of desired purity.

In an alternative embodiment, the benzhydrylamine is protected with the Boc protecting group. Generally, this can be accomplished according to routine methods.

4.2.5. ALTERNATE ROUTE FOR PREPARING THE HANDLE

A benzophenone is prepared as described in Section 4.2.1., supra. The benzophenone can be reduced, e.g., by treatment with sodium borohydride in ethanol or other similar solvent, to yield benzhydryl alcohol. Treatment of the benzhydryl alcohol with a primary amide under acidic conditions results in substitution of the amide for the hydroxy group. This result is analogous to an acylation of a benzhydrylamine.

Preferably the amide group that is chosen is an $N^{\alpha}$-protected amino acid, as described in Section 4.1., supra.

4.3. USE OF THE HANDLE FOR PEPTIDE SYNTHESIS

The handles of this invention are well suited for attaching a peptide chain to a solid phase support for peptide synthesis. The handles can be attached to any amino resins via a suitable functional group, e.g., carboxylic acid, on the hydrocarbon group. Attachment of a carboxylic acid functional group to an amine on the resin can proceed according to any of the techniques commonly used for peptide synthesis, e.g., preparation of an OPfp, HOBt or other activated ester, condensation in the presence of a carbodiimide, etc. These methods are also discussed for synthesis of peptides in Section 4.3.2. Suitable solid supports for use in the invention are discussed, supra.

Solid phase peptide synthesis techniques are well known in the art. Simply put, an $N^{\alpha}$-protected amino acid is activated at the $\alpha$-carbonyl and coupled with the deprotected $N^{\alpha}$ of the nascent peptide-handle-solid phase support. The coupling reactions may be accomplished by techniques familiar to those in the art (see, e.g., Stewart and Young, 1984, Solid Phase Synthesis, Second Edition, Pierce Chemical Co., Rockford, Ill.; Fields and Noble, 1990, "Solid phase peptide synthesis utilizing 9-fluorenylmethyloxycarbonyl amino acids," Int. J. Pept. Protein Res. 35:161–214; Geysen et al., 1987, J. Immunol. Methods 102:259–274). The chemistry of coupling, deprotection, and finally cleavage of the peptide from the solid phase support depends on choice of $\alpha$N-protecting group, which is generally tert-butoxycarbonyl (Boc) or 9-fluorenylmethyloxycarbonyl (Fmoc).

In a preferred embodiment of peptide synthesis using handles of the invention the completeness of coupling should be assessed. Methods of assessing the completeness of coupling are well known in the art. If the coupling was not complete, the reaction should be forced to completion by a second coupling, e.g., (a) by using a higher concentration of the activated amino acid or a different activation mechanism; (b) with the addition of different or additional solvents; or (c) with the addition of chaotropic salts (see Klis and Stewart, 1990, in Peptides: Chemistry, Structure and Biology, Rivier and Marshall (eds.), EDSCOM Publishers, pp. 904–906).

4.3.1. REDUCTION AND CLEAVAGE

After peptide synthesis, the peptide must be cleaved from the solid phase support. If the handle of the invention is in its reduced form, cleavage is accomplished by treatment with acid, for example TFA. Where Fmoc amino acid strategy has been employed, the cleavage will also result in deprotection of the side chains.

Alternatively, when the handle has been used in the oxidized form, either sulfoxide or sulfone, the handle can be reduced to convert it to acid labile handle. Reduction agents known in the art can be used. For example, about 1M trimethylsilylchloride/triphenylphosphine/tetrahydrofuran or more preferably 1M trimethylsilylchloride/triphenylphosphine/dichloromethane can be used to reduce the sulfoxide to the sulfide. Treatment with samarium-iodide (SmI$_2$) will reduce the sulfone and sulfoxide to the sulfide. In yet a further embodiment, the reduction, deprotection and cleavage can be accomplished simultaneously by treatment with silyl bromide. In another embodiment, reduction, deprotection (of Fmoc amino acids) and cleavage-can be accomplished simultaneously by treatment with 1M trimethylsilylbromide/thioanisole/trifluoracetic acid.

A particular advantage of the instant invention is that the amino acid side chains can be deprotected prior to cleavage. In a specific embodiment, infra, the deprotected side chains react to form a cyclic peptide prior to cleavage (see Sections 7.3 and 8., infra). By cyclizing prior to cleavage, side reactions and intermolecular bonding is avoided.

5. EXAMPLE: PREPARATION OF A SOLID SUPPORT WITH A N-FMOC [2-(CARBOXYLATOBUTYL-4-OXY)-4-(METHYLSULFINYL) PHENYL]-[4' (METHYLSULFINYL) PHENYL] METHYLAMINE

5.1. 4,4'-BIS(METHYLTHIO)-2-HYDROXYBENZOPHENONE

A solution of 2-hydroxy-4-methylthiobenzoic acid (45.00 g, 227 mmol) in thionyl chloride (50 ml, 685 mmol) was heated at 40° C. for 15 min with stirring. After addition of 1,2-dichloroethane (EDC) (90 ml) the solution was stirred at 50° C. for 30 min under vacuum (15 mm).

The solid residue was dissolved in EDC (250 ml) at 40° C. and added to the solution of thioanisole (26.7 ml, 227 mmol) in EDC (100 ml). The resulting mixture was cooled to 0° C. and finely ground $AlCl_3$ (33.0 g, 247 mmol) was added portionwise within 75 min at 0°–5° C. The mixture was allowed to warm to 20° C. and the second equivalent of $AlCl_3$ (33.7 g, 253 mmol) was added within 30 min (caution: the temperature rises to 30° C. and the mixture must be cooled). When addition of $AlCl_3$ was finished, the reaction mixture was stirred at 45°–50° C. for 1.5 hr, then cooled down to 20° C. and poured into mixture of ice (300 g) and conc. HCl (180 ml). The organic phase was evaporated and the aqueous layer was heated at reflux for 15 min, cooled down to 20° C. and extracted with EDC (4×150 ml). The collected organic phases were washed with water (3×50 ml), 10% $NaHCO_3$ (2×150 ml), water (1×150 ml), 1M HCl (1×150 ml) and water (2×150 ml) and then were dried over $MgSO_4$. Removal of the solvent in vacuo gave yellow crystals which were recrystallized from EtOH (2100 ml) to give a yellow product (41.00 g, 62%), m.p. 104°–106° C. Anal. Calcd for $C_{15}H_{14}O_2S_2$ (290.41); C 62.04%, H 4.86%, S 22.08%. Found: C 61.86%, H 4.78%, S 22.06%. $^1H$ HMR ($CDCl_3$): 2.51s (3H, $SCH_3$); 2.54s (3H, $SCH_3$); 6.60–6.85m (2H, aromatic); 7.26–7.66m (5H, aromatic); 12.35s (1H, OH). MS-EI: 290($M^+$, 100); 275(20); 243(30); 228(10); 167(40); 151(30); 124(50); 105(10); 77(10); 57(10); 45(10). IR ($CCl_4$):$v_{CO}$ 1620 $cm^{-1}$; $v_{OH}$ 3000 $cm^{-1}$.

5.2. 5-[3-METHYLTHIO-1-OXY-5-(4-METHYLTHIOBENZOYL)PHENYL]-PENTANOIC ACID METHYLESTER

A suspension of alumina (90 g, Fluka-Type 504 C, acid type) and potassium fluoride (dihydrate) (60 g) in water (600 ml) was evaporated to dryness in vacuo. The residue was dried at 135°–140° C. for 24 h to afford 120 g of $KF/Al_2O_3$.

4,4'-Bis(methylthio)-2-hydroxybenzophenone (50.54 g, 174 mmol) was dissolved in acetonitrile (800 ml) at 60° C. The solution was rapidly cooled down to 25° C. and $KF/Al_2O_3$ (127 g) was added all at once. To the stirred suspension methyl bromovalerate (32.4 ml, 226 mmol) was added portionwise within 90 hr and stirring was continued for 120 hr at which time RP HPLC analysis indicated the reaction was complete (Vydac C-18 column, isocratic eluent 75% MeOH, 0.1% TFA, starting compound $R_1$=16 min, product $R_1$=7 min). The suspension was filtered, filtrate cake washed with acetone (2×50 ml) and the filtrate concentrated in vacuo to give yellow product which was used in the next step without further purification. Analytical sample: m.p. 61°–63° C. (EtOH); $R_f$ 0.45 (petroleum ether:EtOAc—60:40). Anal. 61°–63° C. (EtOH); $R_f$ 0.45 (petroleum ether:EtoAc—60:40). Anal. Calcd for $C_{21}H_{24}O_4S_2$ (404.55): C 62.35%, H 5.98%, S 15.85%. Found; C 62.20%, H 6.02%, S 15.62%. $^1H$ NMR ($CDCl_3$): 1.25–1.55m (4H, 2×$CH_2$); 2.15t (2H, $CH_2COO$, $J^3$=7.5 Hz); 2.52s (3H, $SCH_3$); 2.53s (3H, $SCH_3$); 3.64s (3H, $COOCH_3$); 3.90t (2H, $O_4CH_2$, $J^3$=5Hz); 6.79d (1H, $J^4$=1.5 Hz, aromatic); 6.88dd (1H, $J^3$=8 Hz), $J^4$=1.5 Hz, aromatic); 7.18–7.25 m (2H, aromatic); 7.36d (1H, $J^3$=8 Hz, $J^4$=1.5 Hz, aromatic); 7.18–7.25m (2H, aromatic); 7.36d (1H, $J^3$=8 Hz, aromatic); 7.64–7.71m (2H aromatic) EI-MS: 404 ($M^+$, 30); 289(20); 227(40); 167(35); 151(35); 124(20); 115(100); 83(20); 55(40).

5.3 5-[3-METHYLTHIO-1-OXY-5-(4-METHYLTHIOBENZOYL)PHENYL]PENTANOIC ACID

The above prepared crude 5-[3-methylthio-1-oxy-5-(4-methylthiobenzoyl)phenyl]pentanoic acid methylester was dissolved in dioxane (650 ml) and to this solution, 4M NaOH (131 ml, 522 mmol) and methanol (200 ml) were added. The resulting clear solution was stirred overnight at room temperature and then the organic solvents were evaporated in vacuo. The aqueous solution was extracted with ethyl acetate (EtOAc) (2×100 ml) and the aqueous layer was kept in vacuo for 30 min to remove traces of EtOAc. The product was precipitated by slow addition of 20% $H_2SO_4$ (to pH 2), washed with water and dried over $P_2O_5$ in vacuo to give an off-white powder (50.18 g, 87%, based on starting 4,4'-bis (methylthio)-2-hydroxybenzophenone). Analytical sample: m.p. 113°–114° C. (EtOH); $R_f$ 0.22 (petroleum ether:EtOAc-60:40). Anal. Calcd for $C_{20}H_{22}O_4S_2$ (390.52): C 61.55%, H 5.68%, S 16.42%. Found: C 61.15%, H 5.79%, S 16.39%. EI-MS: 390 ($M^+$, 50); 290(90); 243(50); 227(40); 167(100); 151(70); 124(95), 55(60).

5.4. 2-(CARBOXYLATOBUTYL-4-OXY)-4-METHYLTHIO-4'-METHYLTHIOBENZOPHENONE OXIME

A suspension of 5-[3-methylthio-1-oxy-5-(4-methylthiobenzoyl)phenyl]pentanoic acid (18.00 g, 46.1 mmol), anhydrous sodium acetate (9.45 g, 115 mmol) and hydroxylamine hydrochloride (9.60 g, 138 mmol) in 96% ethanol (240 ml) was heated at reflux for 7 hr. After standing overnight at room temperature, the mixture was filtered and concentrated in vacuo to give a white solid, which was used without further purification in the next step. Analytical sample: m.p. 166°–170° C. (EtOH, isomeric mixture); $R_f$ 0.41 ($CHCl_3$:eOH-10:1). EI-MS: 405($M^+$, 2), 387 (25); 300(45); 288(100); 242(30); 227(20); 168(30); 151(40); 124(10); 55(35).

5.5. [2-(CARBOXYLATOBUTYL-4-OXY)-4-(METHYTHIO)PHENYL-4'-METHYLTHIOPHENYL]METHYLAMINE 4-TOLUENESULFONATE

Crude 2-(carboxylatobutyl-4-oxy)-4-methylthio-4'-methylthio-benzophenone oxime (minimum 46.1 mmol) prepared above was placed in a 500 ml Champagne bottle together with powdered zinc (18.37 g, 461 mmol), ethanol (80 ml) and 25% ammonia (240 ml). The suspension was magnetically stirred at 50° C. for 48 hr. After filtration, the filtrate was concentrated in vacuo to give a white solid. After addition of water (300 ml) pH was adjusted to 7 with a saturated solution of toluene sulfonic acid (TsOH) in EtOH and the suspension was filtered. The off-white product was washed with water and then suspended in ethanol (300 ml) at about 60° C. To this suspension, the saturated solution of TsOH in EtOH was added dropwise until the mixture turned to a clear orange solution. Standing in a refrigerator for 48 hr afforded pink crystals, which were suspended by filtration to give the product 1 (18.2 g, 70%), m.p. 178°–180° C. (dec); $R_f$ 0.58 (n-BuOH:AcOH:$H_2O$-80:20:20). FAB-MS: 392(m+1); 375; 275; 227; 137. Anal calcd for $C_{27}H_{33}NO_6S_3$ (563.76); C 57.52%, H 5.9%, N 2.48%, S 17.06%. Found: C 57.87%, H 5.67%, N 2.40%, S 17.11%.

5.6. N-9-Fmoc-{[2-CARBOXYLATOBUTYL-4-OXY)-4-(METHYLSULFINYL) PHENYL-4'-(METHYLSULFINYL)-PHENYL}METHYLAMINE The [2-(carboxylatobutyl-4-oxy)-4-(methylthio) phenyl-4'-methylthiophenyl]methylamine 4'toluenesulfonate (20.00 g, 35.5 mmol) was suspended in the mixture of methanol (320 ml) and water (160 ml). The suspension was heated until the solution became clear, then chilled to 20° C. and a solution of sodium periodate (15.18 g, 71 mmol) in water (140 ml) was added dropwise over a period of 1 hr. The stirring was continued further for 2 hr. The sodium iodate which separated was removed by filtration and the methanol was evaporated in vacuo. The pH of remaining aqueous solution was adjusted to 9 by addition of 4M NaOH and the solution was mixed with acetonitrile (200 ml). The mixture was filtered to remove precipitated inorganic salts and a solution of fluorenylmethyloxycarbonyl-N-hydroxysuccinimidate (Fmoc-succinimidate) (12.99 g, 38.5 mmol) in acetonitrile (80 ml) was added rapidly. The resultant homogenous solution was stirred at 25° C. while adjusting the pH to 8.5–9 with 1M NaOH. After 2 hr no further pH change occurred and the acetonitrile was removed in vacuo. The remaining aqueous solution was diluted with water (100 ml) and extracted with ether (4×50 ml, discarded). The aqueous part was mixed with chloroform (150 ml) and 1M $H_2SO_4$ was added with occasional shaking until the aqueous phase reached pH 2. The aqueous phase was then extracted with chloroform (4×50 ml). The combined organic phases were washed with water (100 ml), dried ($MgSO_4$), and concentrated to give an oil which after dissolving in methanol (150 ml) and standing overnight in refrigerator afforded the product as a white solid. Concentration of mother liquor and addition of ethyl acetate (50 ml) gave the second portion of the product. Yield 14.75 g (65%), m.p. −135°–137° C. $R_f$ ($CHCl_3$:MeOH-9:1)=0.11. $^1H$ NMR ($CDCl_3$): 1.3–1.6m (4H, $CH_2$), 2.17t (2H, $CH_2COO$, J=8 Hz), 2.75s (3H, $SOCH_3$), 2.76s (3H, $SOCH_3$), 3.8–4.05m (2H, $OCH_2$), 4.22t (1H, Fmoc-CH, J=8 Hz), 4.4–4.6m (2H, $CH_2$-Fmoc), 5.95d (1H, $Ar_2CH$, J=9 Hz), 6.25d (1H, NH, J=9 Hz), 7.10–7.80m (15H, aromatic). Anal Calcd for $C_{35}H_{35}NO_7S_2$ (645.8): C 68.10%, H 5.46%, N 2.17%, S 9.93%. Found: C 68.55%, H 5.50%, N 2.11%, S 9.89%.

6. EXAMPLE: ATTACHMENT OF HANDLE ONTO SUPPORT

The solution on N-Fmoc-{[2-(carboxylatobutyl-4-oxy)-4-(methylsulfinyl)phenyl]-4'-(methylsulfinyl)phenyl}methylamine (245 mg, 0.38 mmol), N-hydroxybenzotriazole (52 mg, 0.38 mmol), 4-dimethylaminopyridine (5 mg, 0.038 mmol), and N,N'-diisopropylcarbodiimide (50 μl, 0.38 mmol) in dimethylformamide (10 ml) was added to p-methylbenzhydrylamine (pMBHA) resin (200 mg, 0.076 mmol) (Peptides International, Louisville, Ky.) and the suspension was shaked overnight. The resin was washed with dimethylformamide (5×5 ml) and allowed to react with the solution of acetic acid (46 μl, 0.76 mmol) and N,N'-diisopropylcarbodiimide (119 μl, 0.76 mmol) in dimethylformamide (10 ml) for 5 hr to acetylate the remaining free amino groups. After washing with dimethylformamide (5×5 ml), dichloromethane (5×5 ml), and methanol (5×5 ml) the resin was dried in vacuo. The substitution estimated spectrophotometrically, was 0.34 mmol/g.

7. EXAMPLE: PREPARATION OF PEPTIDES USING THE HANDLE

7.1. H-PHE-PRO-GLN-THR-ALA-ILE-GLY-VAL-GLY-ALA-PRO-$NH_2$

The above prepared resin (132 mg) was used. The general synthetic protocol was as follows: The Fmoc protecting group on the handle was removed with piperidine/dimethylformamide (1:1, v/v, 1×3 min, 1×10 min) followed by washing with dimethylformamide. Boc protecting groups were removed with mixture of trifluoroacetic acid/dichloromethane/anisole (50:50:1, 1×3 min, 1×25 min) followed by washing with dichloromethane. N-Hydroxybenzotriazole active esters were used throughout all synthesis (10 min preactivation). The Boc protecting group was used in the cases of Gly, Val, and Ile amino acids. In the other cases, the Fmoc group was used. The coupling was monitored with bromophenol blue (Krchnak et al., 1988, Collect. Czech. Chem. Commun. 53:2542). Final cleavage from support was accomplished with the mixture of 1Mtrimethylsilylbromide/thioanisole/trifluoroacetic acid (2 hr, 0° C.) followed by dilution with water and extraction with diethyl ether. The crude peptide was obtained in 95% yield (43 mg) and was purified on Sephadex G 25 with 1M acetic acid as eluent. After preparative reverse phase HPLC the pure peptide was obtained in 62% yield (26.6 mg). FAB-MS: 1056 (M+1), 942, 871, 814, 715, 658, 545, 474, 391, 245, 217, 120. Amino acid analysis: Thr (1.00), Gln (1.02), Pro (1.97), Gly (2.00), Ala (1.95), Val (0.97), Ile (0.94), Phe (1.01).

7.2. BOC-TYR-ILE-GLN-ASN-CYS(ClZ-ABU-$O^7BU$)-PRO-LEU-GLY-HANDLE-pMBHA RESIN pMBHA resin prepared analogously as in Example 6 (400 mg, 0.052 mmol) was used for the synthesis of $C^1$-OXT. After each coupling, the remaining free amino groups were acetylated with the mixture of acetic acid/N-hydroxybenzotriazole/N,N'-diisopropylcarbodiimide/N-methylimidazole. The general synthetic protocol used was the same as described in 8.1, supra. All amino acids used were Fmoc-derivatives. Amino acid analysis: Asp(0.98), Glu(1.00), Pro(0.94), Gly(1.13), Cyth(0.54), Ile(0.90), Leu (1.04), Tyr(0.75).

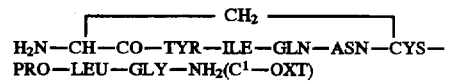

7.3.

Above prepared peptidyl-resin (Section 7.2, supra) (100 mg, 0.012 mmol) was washed with dichloromethane (3×5 ml) and tert-butyl protecting groups were removed with mixture of trifluoroacetic acid/dichloromethane/anisole (50:50:1, 1×3 min, 1×25 min), followed by washing with dichloromethane (5× 5 ml), neutralized with 7% N,N'-diisopropylcarbodiimide/dichloromethane, washed with dichloromethane (3×5 ml) and finally washed with N,N-dimethylformamide (3×5 ml). The cyclization was carried out on the support with N-hydroxybenzotriazole/N,N'-diisopropylcarbodiimide/N,N-dimethylformamide mixture for 24 hr to give a cyclized, fully protected peptide. The final cleavage was accomplished with 1M trimethylsilylbromide/thioanisole/trifluoroacetic acid mixture containing 5% of m-cresole (2 hr, 0° C.). The peptide was precipitated with diethyl ether, filtered, washed with diethyl ether and purified on Sephadex G 25 (1M acetic acid) to give 10.6 mg (89%) of crude product, which was purified on preparative RP-HPLC (Vydac C18) to give 4.5 mg (38%) of a pure $C^1$-OXT. Amino acid analysis: Asp(0.99), Glu(1.00), Pro (0.95), Gly(0.99), Cyth(1.02), Ile(0.96), Leu(1.10), Tyr (0.93), MS(FAB)=990 (M+H).

8. EXAMPLE: TWO-STEP DEPROTECTION OF $C^1$-OXT PRECURSOR

Above prepared peptidyl-resin (Section 7.2, supra) (100 mg, 0.012 mmol) was treated with the mixture of 1M trimethylsilylchloride/triphenylphosphine/tetrahydrofuran (2 ml) at 25° C. for 2 hr. Then the resin was washed with dichloromethane (5×5 ml) and the peptide was cleaved from the resin with the mixture of trifluoroacetic acid/m-cresole (95:5) (2.5 ml) at 25° C. for 30 min. After evaporation to dryness, the peptide was precipitated with diethyl ether to give a powder which was purified on Sephadex G 25 (1M acetic acid) followed by preparative RP-HPLC (Vydac C18) to give 6.5 mg (43%) of a pure $H_2N$-Tyr-Ile-Gln-Asn-Cys (ClZ-Abu-OH)-Pro-Leu-Gly-$NH_2$. Amino acid analysis: Asp(1.04), Glu(1.04), Pro(0.95), Gly(1.03), Cyth(0.94), Ile (0.88), Leu(1.11.), Tyr(0.85), MS (FAB)=1176 (M+H).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A solid phase support comprising a handle for use in peptide synthesis of the general formula (I)

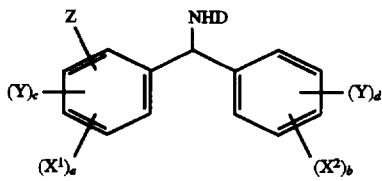

wherein the phenyl group bearing $(X^1)_a$, Z and optionally $(Y)_c$ is referred to as a first phenyl group, and the phenyl group bearing $(X^2)_b$ and optionally $(Y)_d$ is referred to as a second phenyl group;

$X^1$ is selected from the group consisting of —$SR^1$, —$S(O)R^1$, and —$S(O)_2R^1$, each $X^1$ being in an ortho or para position, with respect to the carbon atom of the handle bearing NHD, on the first phenyl group;

$R^1$ is a $C_1$-$C_{10}$ hydrocarbon group;

Z is —$OR^3$, being in an ortho or para position, with respect to the carbon atom of the handle bearing NHD, on the first phenyl group;

$R^3$ is a $C_1$-$C_{10}$ hydrocarbon group substituted with a carboxyl group for coupling to a solid phase support;

$X^2$ is selected from the group consisting of —$SR^2$, —$S(O)R^2$, and —$S(O)_2R^2$, each $X^2$ being in an ortho or para position, with respect to the carbon atom of the handle bearing NHD, on the second phenyl group;

$R^2$ is a $C_1$-$C_{10}$ hydrocarbon group;

Y is —$OR^4$ being in an ortho or para position, with respect to the carbon atom of the handle bearing NHD, not occupied by $(X^1)_a$ or Z on the first phenyl group and in an ortho or para position, with respect to the carbon atom of the handle bearing NHD, not occupied by $(X^2)_b$ on the second phenyl group;

$R^4$ is a $C_1$-$C_{10}$ hydrocarbon group;

a=1–2;
b=1–3;
c=0–1
d=0–1; and

D is selected from the group consisting of —H, a protecting group and an $N^\alpha$-protected aminoacyl, wherein when $X^1$ is —$S(O)R^1$ or —$S(O)_2R^1$, and $X_2$ is —$S(O)$ $R^2$ or —$S(O)_2R^2$, the handle is stable to conditions sufficiently acidic to hydrolyze an Fmoc or a tBoc group from an amine.

2. A solid phase support comprising a handle for use in peptide synthesis of the general formula:

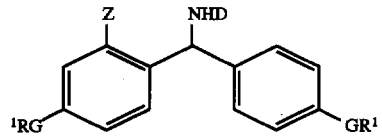

in which Z is —$OR^4$, $R^4$ is a $C_1$-$C_{10}$ hydrocarbon group comprising a carboxyl group for coupling to a solid phase support; $R^1$ is a $C_1$-$C_{10}$ hydrocarbon group and in which each G is independently selected from the group consisting of —S—, —SO—, and —$SO_2$—; and in which D is H, a protecting group or an $N^\alpha$-protected aminoacyl, wherein when each $GR^1$ group is —$S(O)R^1$ or —$S(O)_2R^1$, the handle is stable to conditions sufficiently acidic to hydrolyze an Fmoc or a tBoc group from an amine.

3. A method for preparing a handle for use in peptide synthesis comprising the steps of:

(a) treating a benzoic acid with thionyl chloride to obtain a benzoyl chloride, said benzoic acid having the formula:

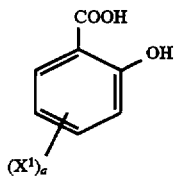

in which a=1 and $(X^1)_a$ is in an ortho or para position with respect to the carboxyl group of the benzoic acid, or a=2 and $(X^1)_a$ is in the ortho and para positions with respect to the carboxyl group of the benzoic acid, $X^1$ is —$SR^1$, and $R^1$ is a $C_1$-$C_{10}$ hydrocarbon group;

(b) mixing the benzoyl chloride prepared in step (a) with a substituted benzene to obtain a mixture, said substituted benzene having the formula:

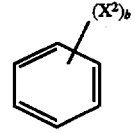

in which b=1 to 3, $X^2$ is —$SR^2$, and $R^2$ is a $C_1$-$C_{10}$ hydrocarbon group;

(c) treating the mixture of step (b) with two molar equivalents of $AlCl_3$ to obtain an ortho-hydroxybenzophenone;

(d) alkylating the —OH group of the ortho-hydroxybenzophenone of step (c) to obtain an ortho-alkoxybenzophenone;

(e) reacting the ortho-alkoxybenzophenone of step (d) with hydroxylamine to yield an oxime derivative of the ortho-alkoxybenzophenone; and (f) reducing the oxime to yield a benzhydrylamine.

4. The method of claim 3 further comprising the following step:

(g) reacting the benzhydrylamine of step (f) with an activated FMOC at about pH 9 in aqueous solution.

5. A method for preparing a resin for peptide synthesis comprising conjugating a handle to a resin to form a resin-handle conjugate, said handle having the general formula (I)

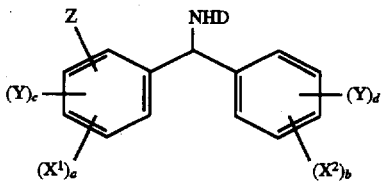

wherein the phenyl group bearing $(X^1)_a$, Z and optionally $(Y)_c$ is referred to as a first phenyl group, and the phenyl group bearing $(X^2)_b$ and optionally $(Y)_d$ is referred to as a second phenyl group;

$X^1$ is selected from the group consisting of —$SR^1$, —$S(O)R^1$, and —$S(O)_2R^1$, each $X^1$ being in an ortho or para position, with respect to the carbon atom of the handle bearing NHD, on the first phenyl group;

$R^1$ is a $C_1$–$C_{10}$ hydrocarbon group;

Z is —$OR^3$, being in an ortho or para position, with respect to the carbon atom of the handle bearing NHD, on the first phenyl group;

$R^3$ is a $C_1$–$C_{10}$ hydrocarbon group substituted with a carboxyl group for coupling to a solid phase support;

$X^2$ is selected from the group consisting of —$SR^2$, —$S(O)R^2$, and —$S(O)_2R^2$, each $X^2$ being in an ortho or para position, with respect to the carbon atom of the handle bearing NHD, on the second phenyl group;

$R^2$ is a $C_1$–$C_{10}$ hydrocarbon group;

Y is —$OR^4$, being in an ortho or para position, with respect to the carbon atom of the handle bearing NHD, not occupied by $(X^1)_a$ or Z on the first phenyl group and in an ortho or para position, with respect to the carbon atom of the handle bearing NHD, not occupied by $(X^2)_b$ on the second phenyl group;

$R^4$ is a $C_1$–$C_{10}$ hydrocarbon group;

a=1–2;

b=1–3;

c=0–1 d=0–1; and

D is selected from the group consisting of —H, a protecting group and an $N^\alpha$-protected aminoacyl, wherein when $X^1$ is —$S(O)R^1$ or —$S(O)_2R^1$, and $X_2$ is —$S(O)R^2$ or —$S(O)_2R^2$, the handle is stable to conditions sufficiently acidic to hydrolyze an Fmoc or a tBoc group from an amine.

6. The method of claim 5 further comprising oxidizing the —$SR^1$ group(s) and —$SR^2$ group(s) of the resin-handle conjugate.

7. A method of peptide synthesis comprising:

(a) oxidizing a handle of the general formula (I)

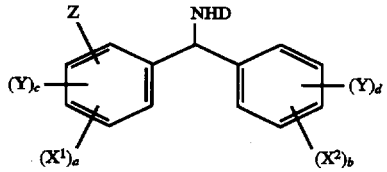

wherein the phenyl group bearing $(X^1)_a$, Z and optionally $(Y)_c$ is referred to as a first phenyl group, and the phenyl group bearing $(X^2)_b$ and optionally $(Y)_d$ is referred to as a second phenyl group;

$X^1$ is selected from the group consisting of —$SR^1$, —$S(O)R^1$, and —$S(O)_2R^1$, each $X^1$ being in an ortho or para position, with respect to the carbon atom of the handle bearing NHD, on the first phenyl group;

$R^1$ is a $C_1$–$C_{10}$ hydrocarbon group;

Z is —$OR^3$, being in an ortho or para position, with respect to the carbon atom of the handle bearing NHD, on the first phenyl group;

$R^3$ is a $C_1$–$C_{10}$ hydrocarbon group substituted with a carboxyl group for coupling to a solid phase support;

$X^2$ is selected from the group consisting of —$SR^2$, —$S(O)R^2$, and —$S(O)_2R^2$, each $X^2$ being in an ortho or para position, with respect to the carbon atom of the handle bearing NHD, on the second phenyl group;

$R^2$ is a $C_1$–$C_{10}$ hydrocarbon group;

Y is —$OR^4$, being in an ortho or para position, with respect to the carbon atom of the handle bearing NHD, not occupied by $(X^1)_a$ or Z on the first phenyl group and in an ortho or para position, with respect to the carbon atom of the handle bearing NHD, not occupied by $(X^2)_b$ on the second phenyl group;

$R^4$ is a $C_1$–$C_{10}$ hydrocarbon group;

a=1–2;

b=1–3;

c=0–1 d=0–1; and

D is selected from the group consisting of —H, a protecting group and an $N^\alpha$-protected aminoacyl, wherein when $X^1$ is —$S(O)R^1$ or —$S(O)_2R^1$, and $X_2$ is —$S(O)R^2$ or —$S(O)_2R^2$, the handle is stable to conditions sufficiently acidic to hydrolyze an Fmoc or a tBoc group from an amine, said handle having a protecting group and —$SR^1$ and —$SR^2$ group(s) to afford a handle having a protecting group and —$S(O)R^1$ and —$S(O)R^2$ groups or —$S(O)_2R^1$ and —$S(O)_2R^2$ groups;

(b) removing the protecting group from the handle of step (a) to afford a deprotected handle;

(c) coupling an activated amino group to the deprotected handle to afford a handle-amino acid conjugate;

(d) successfully coupling at least one activated amino acid to the handle-amino acid conjugate to afford a handle-peptide conjugate;

(e) reducing the —$S(O)R^1$ and —$S(O)R^2$ group(s) or the —$S(O)_2R^1$ and —$S(O)_2R^2$ group(s) of the handle-peptide conjugate; and (f) deprotecting the peptide and cleaving it from the handle.

8. The method of claim 7 in which a step of deprotecting the peptide procedes the reducing step (e).

9. A method for preparing a resin for peptide synthesis comprising conjugating a handle to a resin to form a resin-handle conjugate, said handle having the general formula:

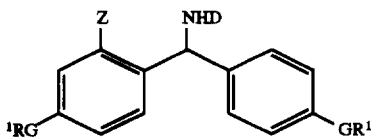

in which Z is —OR$^4$, R$^4$ is a C$_1$–C$_{10}$ hydrocarbon group comprising a carboxyl group for coupling to a solid phase support; R$^1$ is a C$_1$–C$_{10}$ hydrocarbon group and in which each G is independently selected from the group consisting of —S—, —SO—, and —SO$_2$—; and in which D is H, a protecting group or an N$^\alpha$-protected aminoacyl, wherein when each GR$^1$ group is —S(O)R$^1$ or —S(O)$_2$R$^1$, the handle is stable to conditions sufficiently acidic to hydrolyze an Fmoc or a tBoc group from an amine.

10. The method of claim 9 further comprising oxidizing the —SR$^1$ group(s) and —SR$^2$ group(s) of the resin-handle conjugate.

11. A method of peptide synthesis comprising:
(a) oxidizing a handle of the general formula:

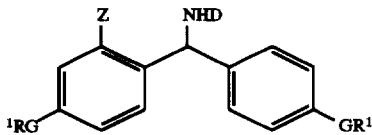

in which Z is —OR$^4$, R$^4$ is a C$_1$–C$_{10}$ hydrocarbon group comprising a carboxyl group for coupling to a solid phase support; R$^1$ is a C$_1$–C$_{10}$ hydrocarbon group and in which each G is independently selected from the group consisting of —S—, —SO—, and —SO$_2$—; and in which D is H, a protecting group or an N$^\alpha$-protected aminoacyl wherein when each GR$^1$ group is —S(O)R$^1$ or —S(O)$_2$R$^1$, the handle is stable to conditions sufficiently acidic to hydrolyze an Fmoc or a tBoc group from an amine, said handle having a protecting group and —SR$^1$ and —SR$^2$ group(s) to afford a handle having a protecting group and —S(O)R$^1$ and —S(O)R$^2$ groups or —S(O)$_2$R$^1$ and —S(O)$_2$R$^2$ groups;

(b) removing the protecting group from the handle of step (a) to afford a deprotected handle;

(c) coupling an activated amino group to the deprotected handle to afford a handle-amino acid conjugate;

(d) successfully coupling at least one activated amino acid to the handle-amino acid conjugate to afford a handle-peptide conjugate;

(e) reducing the —S(O)R$^1$ and —S(O)R$^2$ group(s) or the —S(O)$_2$R$^1$ and —S(O)$_2$R$^2$ group(s) of the handle-peptide conjugate; and (f) deprotecting the peptide and cleaving it from the handle.

12. The method of claim 11 in which a step of deprotecting the peptide precedes the reducing step (e).

* * * * *